United States Patent [19]
Fischell et al.

[11] Patent Number: 6,161,045
[45] Date of Patent: Dec. 12, 2000

[54] METHOD FOR DETERMINING STIMULATION PARAMETERS FOR THE TREATMENT OF EPILEPTIC SEIZURES

[75] Inventors: Robert E. Fischell, Dayton, Md.; David R. Fischell, Fair Haven, N.J.; Martha J. Morell, Irvington, N.Y.; Barbara Gibb, Columbia, Md.

[73] Assignee: NeuroPace, Inc., Sunnyvale, Calif.

[21] Appl. No.: 09/323,407

[22] Filed: Jun. 1, 1999

[51] Int. Cl.[7] .................................................. A61N 1/36
[52] U.S. Cl. ............................................................... 607/45
[58] Field of Search .............................. 607/45; 600/378

[56] References Cited

U.S. PATENT DOCUMENTS

| | | | |
|---|---|---|---|
| 3,850,161 | 11/1974 | Lis | 607/45 |
| 4,735,208 | 4/1988 | Wyler et al. | 600/378 |
| 5,797,965 | 8/1998 | Spano et al. | 607/45 |

Primary Examiner—William E. Kamm

[57] ABSTRACT

Disclosed is a method for determining the optimal electrical stimulation parameters for intracranial stimulation therapy before implantation of a device for electrical stimulation therapy for epilepsy. This method would be used during intracranial electrical stimulation and monitoring procedures which are currently used to identify an epileptic region and map regional brain function prior to resective surgery. This method is used to determine therapeutic stimulation parameters during an evaluation procedure that can be carried out prior to the implantation of a closed-loop electrical stimulation device that is responsive to the onset of an epileptic seizure.

16 Claims, 2 Drawing Sheets

METHOD FOR DETERMINING STIMULATION PARAMETERS FOR THE TREATMENT OF EPILEPTIC SEIZURES

FIELD OF USE

This invention is in the field of methods for the treatment of neurological disorders in human subjects, particularly those disorders that originate in the brain.

BACKGROUND OF THE INVENTION

It is well known that in certain patients epileptic seizures consistently originate from a single location within the brain. When a primary epileptogenic region or seizure focus is suspected, some form of monitoring by implanted electrodes may be performed during which time the electrodes are connected to recording instruments such as an electroencephalograph (EEG) machine. Additionally, in some patients, intracranial electrical stimulation using implanted electrodes is performed to map regional brain function as a precursor to surgical excision of the epileptogenic region. During the mapping procedure, the stimulation will often induce seizures or seizure-like after discharges from the epileptogenic region.

Electrical stimulation therapy is an alternative to resective surgery. To be most effective in using electrical stimulation as a therapy, the electrode location(s) and electrical pulse parameters must be adapted to each patient. Existing devices for electrical stimulation therapy, such as the Cyberonic's NeuroCybernetic Prosthesis System and the Medtronic Activa System, have the capability for adjusting stimulation parameters only after surgical implantation of the therapeutic device. This means that considerable expense and patient associated risks are incurred before it is known that the device will be therapeutic or how well it will function after it is implanted.

SUMMARY OF THE INVENTION

The disclosed invention is a method for determining the optimal electrical stimulation parameters for intracranial stimulation therapy before implantation of a device for electrical stimulation therapy. This method would be used during intracranial electrical stimulation and monitoring procedures which are currently used to identify the epileptogenic region and map regional brain function prior to resective surgery. The present invention method is novel in that, unlike prior art methods, it is adapted to determine therapeutic stimulation parameters during an evaluation procedure that can be carried out prior to the implantation of an electrical stimulation device. Such an evaluation procedure would be especially useful for determining the parameters for a closed-loop stimulation device that is responsive to the onset of epileptic seizures such as is described in U.S. patent application Ser. No. 08/957,869, now U.S. Pat. No. 6,016,449, by Fischell et al.

During standard intracranial electrical stimulation and monitoring procedures, electrical stimulation is applied to one or more of an array of electrodes placed under the patient's cranium to map the regional brain function to assess the suitability of resective surgery. Seizure-like after discharges or actual clinical seizures can be induced by this stimulation. The EEG signal that is seizure-like either from this standard intracranial electrical stimulation or from a natural epileptic seizure is called "epileptiform activity". The reproducibility of such artificially created epileptiform activity makes them ideally suited for use in optimizing electrical stimulation therapy parameters for aborting epileptic seizures.

The apparatus to perform this method includes an EEG analysis workstation for monitoring the patient's brain function and localizing epileptiform activity. The apparatus also includes an electrical stimulator to both evoke epileptiform activity (i.e., after discharges) and provide responsive stimulation therapy. It is envisioned that a multiplicity of brain electrodes could be used both for monitoring, localizing and applying electrical stimulation. The present invention method includes the following steps:

1. During a patient's intracranial electrical stimulation and monitoring procedure, natural epileptiform activity is identified and localized to specific brain electrodes using the EEG analysis workstation. This method is well known to epileptologists.
2. Manual electrical stimulation is applied to specific electrodes to induce an after discharge type of seizure (i.e., epileptiform activity) from the epileptogenic region of the patient's brain. This requires empirical testing of various stimulation parameters until epileptiform activity is evoked.
3. Stimulation that is identical to that which caused the epileptiform activity is immediately reapplied to the same specific electrodes used in step 2. If the epileptiform activity seizure activity is aborted by applying a specific type of electrical stimulation (as compared with after discharges seizure activity where no second electrical stimulation is applied), go to step 5.
4. If the epileptiform activity is not aborted, adjust the stimulation parameters until it is; then go to step 5. If the epileptiform activity cannot be aborted, then the patient may not be a candidate for electrical stimulation therapy.
5. Save the information on stimulation parameters and specific electrode placement for use in programming an implantable electrical stimulation therapy device and final placement of the brain electrodes.

An additional step of testing the stimulation parameters on naturally occurring seizures can be added, but this is practical only if naturally occurring seizures are comparatively frequent. It is also envisioned that an automated system could be used to detect the epileptiform activity and automatically respond rather than having the reapplication of electrical stimulation done manually.

It is also envisioned that with the present invention method, the intracranial stimulation electrodes used to abort the epileptiform activity can be different from the stimulation electrodes used to evoke the epileptiform It is also envisioned that with the present invention method, the frequency and amplitude (i.e. energy) of the electrical pulse(s) used to abort the epileptiform activity can be different from the frequency and amplitude of the electrical pulse that is used to create the after discharge activity.

It is also envisioned that with the present invention method, the evoking electrical stimulation used to induce the epileptiform activity is first tried at low amplitude and increased in steps until an after discharge (i.e., epileptiform activity) is evoked or a preset limit is reached.

It is also envisioned that with the present invention method, the electrical stimulation used to abort the epileptiform activity is first tried at low amplitude and then increased in steps until an after discharge (i.e., epileptiform activity) is aborted or a preset limit is reached. It should be understood that epileptiform activity is an EEG signal that is associated with an epileptic seizure. For the purposes of the present invention, "aborted epileptiform activity" is defined as epileptiform activity that has been completely stopped or has had a significant reduction in amplitude or duration as compared to either natural or evoked epileptiform activity of that patient.

Thus it is an object of the present invention method to use patient specific electrical stimulation parameters that successfully control evoked epileptiform activity as the stimulation parameters for an electrical stimulation therapy device used to control natural epileptiform activity.

Another object of the present invention method is to use the specific electrode locations identified during an intracranial electrical stimulation and monitoring procedure as the electrode locations for an electrical stimulation therapy device to control natural epileptiform activity.

Still another object of the present invention method is to have the intracranial stimulation electrodes used to responsively abort evoked epileptiform activity be the same as the stimulation electrodes used to evoke the after discharge epileptiform activity.

Still another object of the present invention method is to have the intracranial stimulation electrodes used to responsively abort evoked epileptiform activity be different from the stimulation electrodes used to evoke the epileptiform activity.

Yet another object of the present invention method is to have the frequency, pulse duration and amplitude of the electrical pulse(s) used to control the evoked epileptiform activity be the same as the frequency, pulse duration and amplitude of the evoking electrical pulses.

Yet another object of the present invention method is to have the frequency, pulse duration and amplitude of the electrical pulse(s) used to control the evoked epileptiform activity be different from the frequency, pulse duration and amplitude of the evoking electrical pulses.

Yet another object of the present invention method is to have the evoking electrical stimulation used to evoke epileptiform activity be first tried at low amplitude and then increased in steps until epileptiform activity is evoked or a preset upper limit is reached.

Yet another object of the present invention method is to have the electrical stimulation used to abort evoked epileptiform activity be first tried at low amplitude and then the amplitude is increased in steps until the evoked epileptiform activity is controlled or a preset upper limit is reached.

Yet another object of the present invention method is to have the electrical stimulation used to abort natural epileptiform activity be first tried at low amplitude and increased in steps until the natural epileptiform activity is aborted or a preset level is reached.

These and other objects and advantages of this invention will become obvious to a person of ordinary skill in this art upon reading of the detailed description of this invention including the associated drawings as presented herein.

DETAILED DESCRIPTION OF THE DRAWINGS

Figure 1:
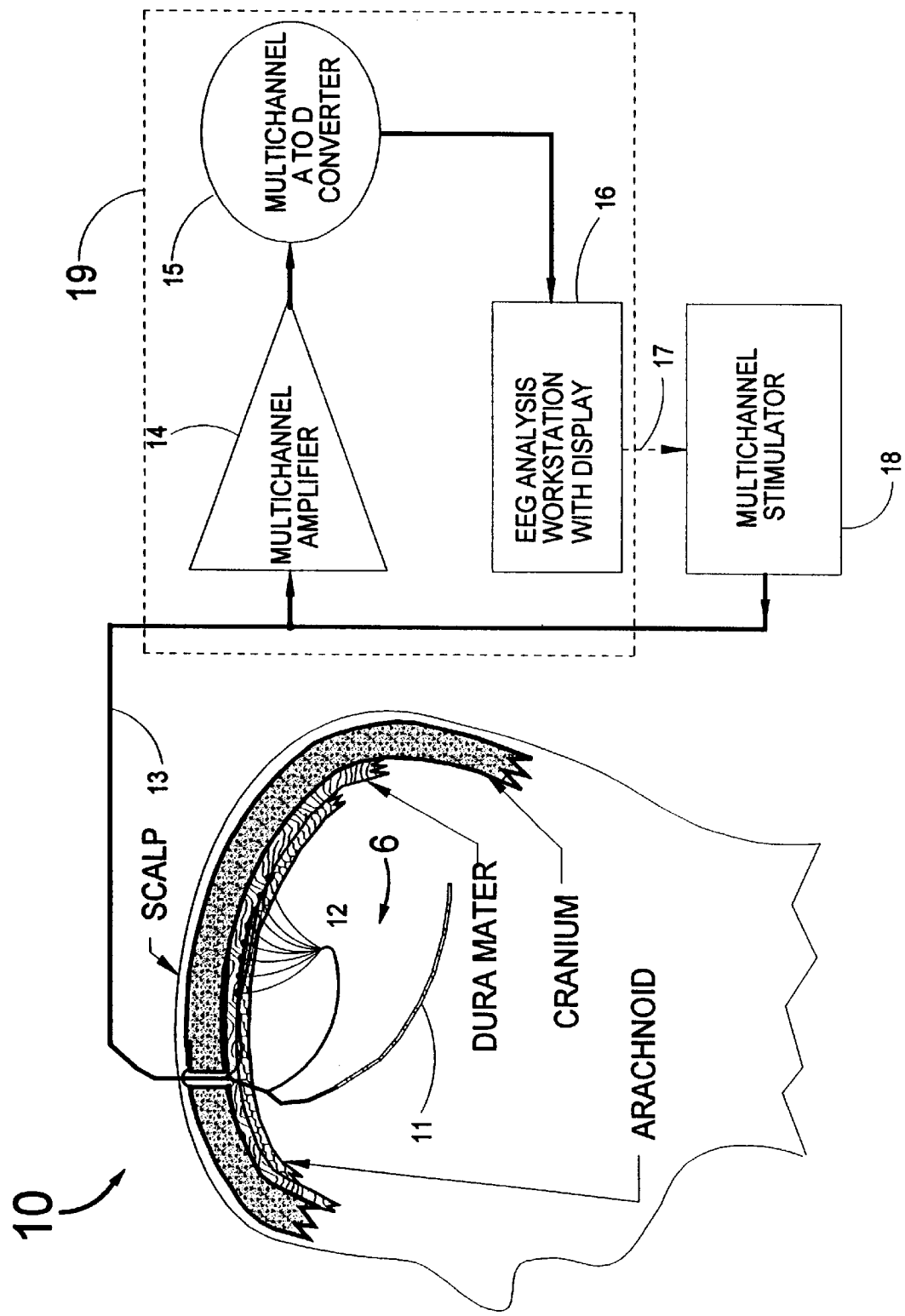
FIG. 1 is a block diagram of the epileptiform activity monitoring and control system used to determine an optimal set of electrical stimulation parameters to abort a patient's epileptic seizures

FIG. 1 is a block diagram of the epileptiform activity monitoring and control system 10 used to determine an optimal set of electrical stimulation parameters to control a patient's epileptic seizures. A multiplicity of depth electrodes 11 are implanted deep into the patient's brain. Intracerebral depth electrodes 11, which are often line arrays of electrodes, are useful for recording from or stimulating deep cerebral structures such as the amygdala, hippocampus, cingulate and orbital-frontal regions. These deep cerebral structures are characteristically involved in many medically refractory partial epilepsies.

An array of brain surface electrodes 12 is placed above the surface of the patient's brain and may contain more than 100 electrodes. Brain electrodes 6 include both the depth electrodes 11 and brain surface electrodes 12. The brain electrodes 6 may also include electrodes placed elsewhere under the patient's scalp near or within the brain.

A multi-strand electrode cable 13 connects the depth electrodes 11 and surface electrodes 12 to a multichannel amplifier 14. After amplification, the multiple channels are digitized by an A to D converter 15 and passed on to an EEG analysis workstation 16. The workstation 16 has the capability to process, store, play back and display on a monitor the patient's EEG signals. The workstation 16 also has the capability to detect epileptiform activity. The multichannel amplifier, A to D converter and EEG analysis workstation together comprise the EEG analysis system 19.

A multichannel electrical stimulator 18 is also connected to the multi-strand cable 13 allowing selective stimulation on any of the depth electrodes 11 or surface electrodes 12. For much of the procedure used to determine an optimal set of stimulation parameters to control a patient's epileptic seizures, the stimulator 18 is actuated manually by the physician. By using the interface 17, the EEG analysis workstation 16 can be adapted to automatically initiate stimulation. Typical stimulation frequencies are between 20 and 100 Hz and typical durations of a sequence of electrical stimulation pulses are between 0.25 and 5 seconds. Bipolar pulses of duration between 1 and 100 ms with pulse current amplitudes between 0.5 and 15 mA are typical.

Multichannel EEG amplifiers such as the Synamps from NeuroScan, Inc. are commercially available with built in analog to digital converters designed to interface to a Windows PC which performs the functions of the EEG analysis workstation 16. Software for EEG analysis and display is also commercially available. This software can be used to process, store, play back and display on a monitor in real time the patient's EEG signals. Electrical stimulators are also commercially available and are commonly used by neurologists for brain mapping procedures with implanted deep and/or surface electrodes.

Figure 2:
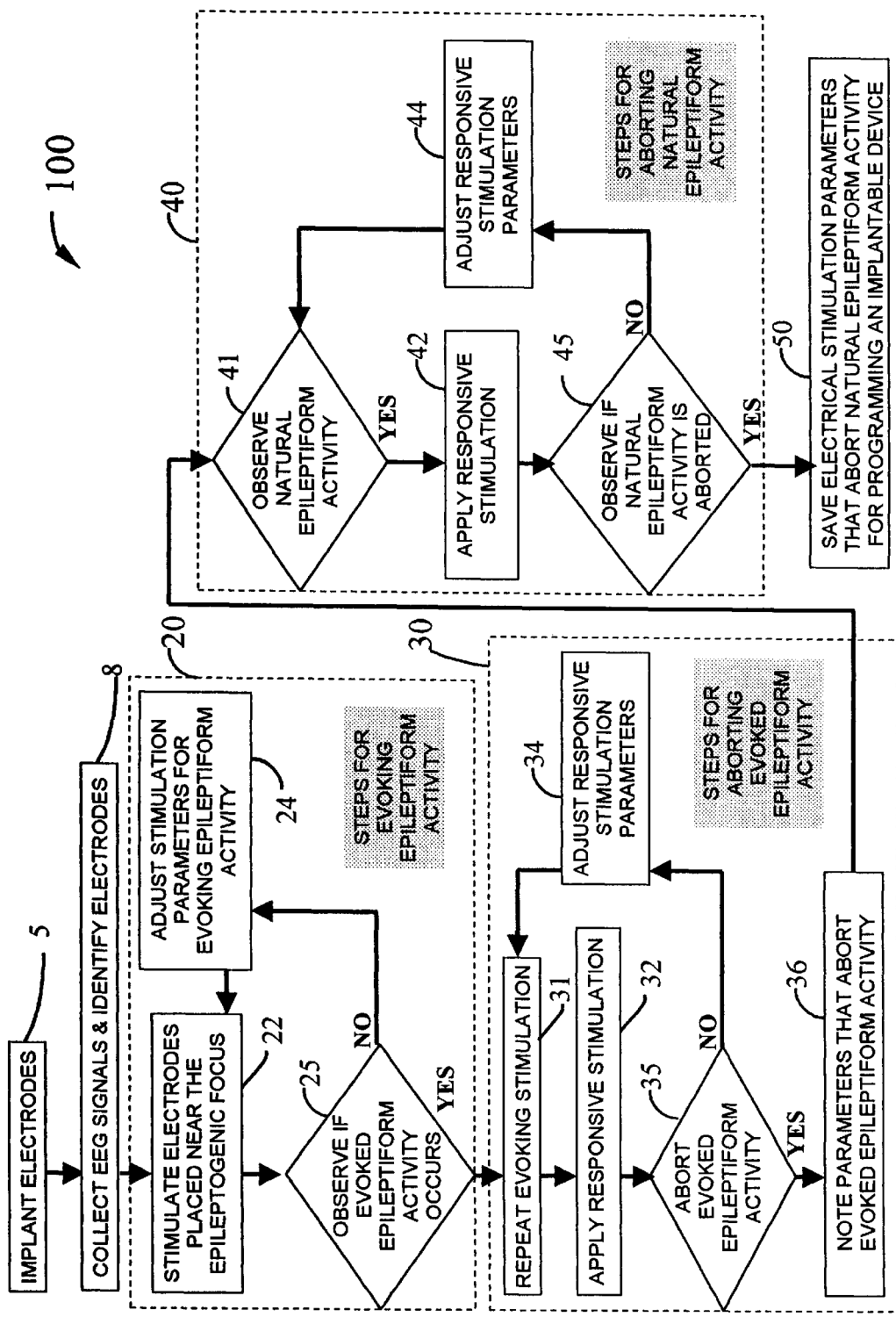
FIG. 2 is a flowchart of the method showing steps in the method of the present invention used to determine an optimal set of stimulation parameters to abort a patient's epileptic seizures.

The procedure used to determine an optimal set of stimulation parameters to control a patient's epileptic seizures using the apparatus of FIG. 1 is diagrammed in FIG. 2. FIG. 2 is a flowchart showing steps in the method 100 of the present invention used to determine an optimal set of stimulation parameters to abort a patient's epileptic seizures.

The method 100 comprises the following steps:
1. Implanting brain electrodes including depth electrodes 11 and surface electrodes 12 as shown in FIG. 1. The IMPLANT ELECTRODES step 5 is shown at the start of FIG. 2. The brain electrodes 11 or 12 may be implanted as a two dimensional surface array either epidurally or sub-durally or may be a line array placed deep into brain tissue at sites such as the hippocampus or thalamus.
2. Identifying a subset of the electrodes 6 that best show epileptogenic activity using the EEG analysis system 19 of FIG. 1. This is the step 8, COLLECT EEG SIGNALS & IDENTIFY ELECTRODES of FIG. 2.

3. Applying electrical stimulation to the subset of the electrodes 6 identified in step 2 above. This is the step 22, STIMULATE ELECTRODES PLACED NEAR THE EPILEPTOGENIC FOCUS of FIG. 2. This is the first step in the methodology consisting of a series of STEPS FOR EVOKING EPILEPTIFORM ACTIVITY 20 of FIG. 2.

4. Observing epileptiform activity which is the step 25, OBSERVE IF EVOKED EPILEPTIFORM ACTIVITY OCCURS. If epileptiform activity is not found, adjusting stimulation parameters which is the step 24, ADJUST STIMULATIOIN PARAMETERS FOR EVOKING EPILEPTIFORM ACTIVITY and applying again the evoking electrical stimulation until epileptiform activity is induced.

5. Applying the step 31, REPEAT EVOKING STIMULATION using those electrical stimulation parameters that were determined using the STEPS FOR EVOKING EPILEPTIFORM ACTIVITY 20. This is the start of a methodology which are the STEPS FOR ABORTING EVOKED EPILEPTIFORM ACTIVITY 30 whose goal is to abort evoked epileptiform activity.

6. When epileptiform activity is again created, applying responsive stimulation with the same stimulation parameters and to the same electrodes that induced the epileptiform activity. This is the step 32, APPLY RESPONSIVE STIMULATION.

7. Observing if the epileptiform activity is stopped. This is the step 35, ABORT EVOKED EPILEPTIFORM ACTIVITY.

8. If the epileptiform activity is not aborted, then adjusting the responsive stimulation parameters and/or choice of electrodes for applying the responsive stimulation until the evoked epileptiform activity is aborted. This is the step 34, ADJUST RESPONSIVE STIMULATION PRAMETERS. Once the evoked epileptiform activity has been aborted, the responsive stimulation parameters comprising amplitude, frequency, duty cycle and choice of stimulation electrodes are noted. This is the step 36, NOTE PARAMETERS THAT ABORT EVOKED EPILEPTIFORM ACTIVITY.

9. The patient is now ready for the methodology consisting of the STEPS FOR ABORTING NATURAL EPILEPTIFORM ACTIVITY 40 of FIG. 2. For these STEPS 40, the system 10 of FIG. 1 is used to monitor EEG activity looking to OBSERVE NATURAL EPILEPTIFORM ACTIVITY which is step 41 of FIG. 2. This is the first step in aborting naturally occurring epileptic seizure activity using electrical stimulation parameters that were determined from the stopping of evoked epileptiform activity.

11. Applying responsive stimulation is then accomplished to see if the naturally occurring epileptiform activity can be aborted. This is the step 42, APPLY RESPONSIVE STIMULATION.

12. Observing if the naturally occurring epileptiform activity is aborted is then accomplished. This is the step 45, OBSERVE IF NATURAL EPILEPTIFORM ACTIVITY IS ABORTED.

13. If the naturally occurring epileptiform activity is not aborted, then adjusting the responsive stimulation parameters and/or choice of electrodes for applying the responsive stimulation. This is the step 44, ADJUST RESPONSIVE STIMULATION PARAMETERS. This procedure is repeated until stimulation parameters and/or the choice of electrodes provides successful aborting of natural epileptiform activity.

14. Saving the successful stimulation parameters and choice of electrodes from the STEPS 40. This is the step 50, SAVE ELECTRICAL STIMULATION PARAMETERS THAT ABORT NATURAL EPILEPTIFORM ACTIVITY FOR PROGRAMMING AN IMPLANTABLE DEVICE.

Thus, using the method 100, parameters have been determined that can be used to program an implantable device (a neuropacemaker) for the treatment of epileptic seizure activity using electrical stimulation that is responsive to the early detection of natural epileptiform activity. Furthermore, if the method 100 successfully aborts the patient's natural seizures, then there is a high level of confidence that an implanted neuropacemaker system using those same electrodes and electrical stimulation parameters will also be successful in aborting the patient's seizure activity. It should be noted that the responsive stimulation should be applied within 10 seconds of the start of the evoked epileptiform activity and ideally within 10 second of the evoked epileptiform activity.

The evoking electrical stimulation can be applied to any one, several, or all electrodes of the multiple brain electrodes 6 of FIG. 1. The responsive electrical stimulation can also be applied to any one, several, or all electrodes of the multiple brain electrodes 6 of FIG. 1. The evoking electrical stimulation as sent to each one of the responsive electrodes car be programmed to be identical or different from one electrode to another in amplitude, frequency, waveform, pulse duration, or time duration of the sequence of electrical stimulation pulses. The responsive electrical stimulation signals sent to each responsive electrode can also be identical to or they can be programmed to be different from one electrode to another in amplitude, frequency, waveform, pulse duration, or time duration of the sequence of electrical stimulation pulses. The responsive electrical stimulation sent to each responsive electrode can be identical to the evoking electrical stimulation or they can differ in any one or all of the stimulation parameters.

Examples of the iterative methods for incremental stimulation increases for each of the steps 20, 30 and 40 of FIG. 2 are described below.

In the STEPS FOR EVOKING EPILEPTIFORM ACTIVITY 20, the evoking electrical stimulation can first be applied at an amplitude of less than 15 mA, typically less than 5.0 mA and possibly as low as 0.5 mA. If no evoked epileptiform activity occurs, the stimulation parameters are adjusted such that the amplitude is increased by an increment such as 0.5 mA and the evoking stimulation is reapplied. With each iteration where control does not occur, the amplitude is increased by an increment such as 0.5 mA until the epileptiform activity is evoked or an upper current limit such as 15 mA is reached.

In the STEPS FOR ABORTING EVOKED EPILEPTIFORM ACTIVITY 30, the responsive stimulation can first be applied at an amplitude of less than 15 mA, typically less than 5 mA and possibly as low as 0.5 mA and whether or not the epileptiform activity is aborted can be discerned. If no control of the evoked epileptiform activity occurs, the responsive stimulation parameters are adjusted such that the amplitude is increased by an increment such as 0.5 mA and the responsive stimulation is reapplied. With each iteration where control does not occur, the responsive stimulation amplitude is increased by some increment such as 0.5 mA until the evoked epileptiform activity is controlled or an upper current limit such as 15 mA is reached.

In the STEPS FOR ABORTING NATURAL EPILEPTIFORM ACTIVITY, 40, responsive electrical stimulation can first be applied at an amplitude of less than 15 mA, typically less than 5.0 mA and possibly as low as 0.5 mA and the aborting of natural epileptiform activity can be discerned. If no control of the natural epileptiform activity occurs, the responsive stimulation parameters are adjusted such that the amplitude is increased by an increment such as 0.5 mA and the responsive stimulation is reapplied when the next natural epileptiform activity occurs. With each iteration where control does not occur, the responsive stimulation amplitude can be increased by 0.5 mA increments until the natural epileptiform activity is aborted or an upper current limit such as 15 mA is reached.

Various other modifications, adaptations, and alternative designs are of course possible in light of the above teachings. Therefore, it should be understood at this time that within the scope of the appended claims the invention might be practiced otherwise than as specifically described herein.

What is claimed is:

1. A method for selecting electrical stimulation parameters to abort epileptiform activity of a human subject, the method comprising the following steps:

(a) placing a multiplicity of brain electrodes beneath the scalp of the human subject and connecting the brain electrodes to an EEG analysis system that is adapted to display EEG signals from the electrodes;

(b) collecting and analyzing the EEG signals from the brain electrodes with the EEG analysis system and selecting electrodes that are located in close proximity to an epileptogenic focus of the human subject;

(c) connecting the brain electrodes to an electrical stimulator, the electrical stimulator being adapted to provide a sequence of electrical stimulation pulses that are programmable with respect to at least one of the following parameters: pulse amplitude, pulse frequency, pulse waveform, pulse duration, and time duration of the sequence of electrical stimulation pulses;

(d) applying an electrical stimulation signal from the electrical stimulator to the at least two brain electrodes, which electrical stimulation signal is an evoking electrical stimulation;

(e) adjusting the programmable parameters of the evoking stimulation and reapplying the evoking electrical stimulation until evoked epileptiform activity is seen with the EEG analysis system;

(f) reapplying the evoking electrical stimulation that induced epileptiform activity and when the epileptiform activity is observed, then applying within a time period of less than 10 seconds a responsive electrical stimulation for aborting the epileptiform activity.

2. The method of claim 1 wherein the responsive electrical stimulation parameters are generally the same as the evoking electrical stimulation parameters.

3. The method of claim 1 wherein the responsive electrical stimulation parameters have an increased pulse amplitude as compared to the pulse amplitude used to evoke epileptiform activity.

4. The method of claim 1 further comprising the step of iterative modification of the responsive electrical stimulation parameters of the responsive electrical stimulation until the evoked epileptiform activity is aborted.

5. The method of claim 4 wherein the iterative modification of stimulation parameters comprises the initial application of responsive electrical stimulation having a pulse amplitude of less than 15 mA and subsequent responsive electrical stimulation being applied with an increasing steps of pulse amplitude until epileptiform activity is aborted.

6. The method of claim 5 wherein the initial pulse amplitude for the responsive electrical stimulation is less than 5.0 mA.

7. The method of claim 1 wherein each pulse of the sequence of electrical stimulation pulses is a bipolar pulse.

8. The method of claim 7 wherein the duration of each bipolar pulse is between 1.0 and 100 milliseconds.

9. The method of claim 1 wherein the frequency of the pulses in the sequence of electrical stimulation pulses is between 20 and 100 Hz.

10. The method of claim 1 further comprising the step of applying an evoking electrical stimulation with a pulse amplitude of less than 15 mA and subsequently increasing the pulse amplitude until epileptiform activity is induced.

11. The method of claim 10 wherein the initial pulse amplitude of the evoking electrical stimulation is less than 5.0 mA.

12. The method of claim 1 further comprising the step of observing with the EEG analysis system when the human subject undergoes natural epileptiform activity.

13. The method of claim 12 further comprising the step of applying a sequence of electrical stimulation pulses to abort the natural epileptiform activity.

14. The method of claim 13 wherein the sequence of electrical stimulation pulses to abort the natural epileptiform activity is generally the same as the responsive electrical stimulation pulses used for aborting evoked epileptiform activity.

15. The method of claim 13 further comprising the step of recording the electrical stimulation parameters of the sequence of electrical stimulation pulses that aborted the natural epileptiform activity for use in setting the electrical stimulation parameters of an implantable electrical stimulator.

16. The method of claim 1 wherein the multiplicity of electrodes are placed beneath the cranium of the human subject.

* * * * *